United States Patent [19]

Tews et al.

[11] Patent Number: 5,501,063
[45] Date of Patent: Mar. 26, 1996

[54] APPARATUS AND METHOD OF REDUCING THE FORCE TO EXPEL A TAMPON FROM A TAMPON APPLICATOR AND THE APPLICATOR ITSELF

[75] Inventors: Richard R. Tews, Larsen; Jeffrey M. Weyenberg, Appleton; Noel J. Rasmussen, Oshkosh, all of Wis.

[73] Assignee: Kimberly-Clark Corporation, Neenah, Wis.

[21] Appl. No.: 301,220

[22] Filed: Sep. 6, 1994

[51] Int. Cl.⁶ .......................... A61F 13/30; A61F 15/00; B29C 17/00
[52] U.S. Cl. .................. 53/452; 53/141; 53/558; 493/271; 493/293; 493/308; 604/14
[58] Field of Search .................. 53/452, 468, 396, 53/141, 50, 133.1, 558, 577, 575, 578, 236; 425/340, 343, 341; 493/308, 271, 293, 409, 338, 339; 604/14, 15, 16

[56] References Cited

U.S. PATENT DOCUMENTS

| | | | |
|---|---|---|---|
| 1,181,965 | 5/1916 | Bohlman. | |
| 2,178,840 | 11/1939 | Lorenian | 128/260 |
| 2,298,752 | 10/1942 | Crockford | 128/263 |
| 2,639,646 | 5/1953 | Thompson et al. | 93/36.5 |
| 2,916,975 | 12/1959 | Gasior et al. | 93/55.1 |
| 3,078,025 | 2/1963 | Welshon | 229/1.5 |
| 3,087,390 | 4/1963 | Ruza | 93/36.5 |
| 3,141,595 | 7/1964 | Edwards | 229/1.5 |
| 3,164,314 | 1/1965 | Waycie | 229/1.5 |
| 3,203,611 | 8/1965 | Anderson et al. | 229/1.5 |
| 3,204,635 | 9/1965 | Voss et al. | 128/263 |
| 3,312,383 | 4/1967 | Shapiro et al. | 229/1.5 |
| 3,347,234 | 10/1967 | Voss | 128/260 |
| 3,433,225 | 3/1969 | Voss et al. | 128/263 |
| 3,572,339 | 3/1971 | Voss et al. | 128/260 |
| 3,575,169 | 4/1971 | Voss | 128/263 |
| 3,581,744 | 6/1971 | Voss | 128/263 |
| 3,676,543 | 7/1972 | Reinhold et al. | 264/296 |
| 3,696,812 | 10/1972 | Jaycox | 128/263 |
| 3,805,786 | 4/1974 | Bernardin et al. | 128/263 |
| 3,807,399 | 4/1974 | Morman et al. | 128/263 |
| 4,104,013 | 8/1978 | Kelly et al. | 425/324.1 |
| 4,215,087 | 7/1980 | Mathison | 264/320 |
| 4,298,331 | 11/1981 | Mueller | 425/393 |

(List continued on next page.)

FOREIGN PATENT DOCUMENTS

| | | |
|---|---|---|
| 2095390 | 11/1993 | Canada. |
| 35-27595 | 10/1960 | Japan. |
| 1012217 | 12/1965 | United Kingdom. |
| 1484912 | 9/1977 | United Kingdom. |

Primary Examiner—James F. Coan
Attorney, Agent, or Firm—Thomas J. Connelly

[57] ABSTRACT

An apparatus and method are disclosed for reducing the force required to expel a catamenial tampon from a tampon applicator. The tampon applicator is also disclosed. The tampon applicator includes a first member which is capable of housing an absorbent tampon. The first member has an inside diameter, first and second spaced apart ends, and an insertion tip formed adjacent to the first end. The insertion tip at least partially closes the first end of the first member and facilitates insertion of the tampon applicator into a woman's vagina. The insertion tip is opened, expanded and reclosed prior to positioning the tampon in the first member. This action allows the insertion tip to be reopened with a minimum amount of expulsion force. The apparatus includes a first punch having an outside diameter which is sized slightly less than the inside diameter of the first member. This enables the first punch to slide within the first member from the second end toward the first end. The first punch has a forward end which is capable of opening the insertion tip. The apparatus also includes a second punch having a forward end with an outside diameter which is sized larger than the inside diameter of the first member. The second punch is capable of entering the opened insertion tip and expanding at least a portion of the inside diameter thereof. The method discloses using the above mentioned apparatus as well as the step of reclosing the insertion tip such that a reduced force is required to reopen the insertion tip and expel the tampon.

28 Claims, 3 Drawing Sheets

U.S. PATENT DOCUMENTS

| | | | |
|---|---|---|---|
| 4,302,174 | 11/1981 | Hinzmann | 425/341 |
| 4,412,833 | 11/1983 | Wiegner et al. | 604/14 |
| 4,453,925 | 6/1984 | Decker | 604/14 |
| 4,479,791 | 10/1984 | Sprague | 604/14 |
| 4,508,531 | 4/1985 | Whitehead | 604/14 |
| 4,650,459 | 3/1987 | Sheldon | 604/15 |
| 4,778,374 | 10/1988 | Takahashi et al. | 425/343 |
| 4,846,802 | 7/1989 | Sanders, III | 604/15 |
| 5,184,995 | 2/1993 | Kuchenbecker | 493/79 |
| 5,279,541 | 1/1994 | Frayman et al. | 604/14 |
| 5,290,501 | 3/1994 | Klesius | 264/322 | ns
APPARATUS AND METHOD OF REDUCING THE FORCE TO EXPEL A TAMPON FROM A TAMPON APPLICATOR AND THE APPLICATOR ITSELF

FIELD OF THE INVENTION

This invention relates to an apparatus and method of reducing the force required to expel a catamenial tampon from a tampon applicator. More specifically, this invention relates to a tampon applicator having an insertion tip which requires a minimum amount of force to expel a catamenial tampon therefrom.

BACKGROUND OF THE INVENTION

Catamenial tampons and other types of absorptive media are routinely inserted into body cavities, such as a woman's vagina, to absorb menstrual fluid, blood and other kinds of body fluid. One convenient way to position such absorbent tampons into a body cavity is through the use of an applicator. Comfortable and clean insertion of the absorbent tampon are keys to repeated sale of such applicators.

Tampon applicators are available in a variety of shapes and sizes. One piece and two piece applicators are known, with the two piece telescopically assembled design being the most prevalent. The one piece applicator consists of a hollow tube which houses an absorbent tampon. The applicator is designed to have the user insert the tube into her vagina and then use one of her fingers to expel the tampon into her vagina. In the two piece tampon applicator, the tampon is housed in an outer tube and is expelled into a woman's vagina by an inner member which is telescopically mounted therein and acts as a plunger.

Some tampon applicators utilize a hollow tube having an open insertion end through which the tampon is always exposed while other applicators utilize a completely closed or partially closed design. The partially or fully closed insertion tips are preferred, for they facilitate insertion of the outer tube into the woman's vagina and also prevent premature contamination of the absorbent tampon. The insertion tip can be formed from a thin film membrane or consist of a plurality of flexible petals, folds or pleats. The petals and pleats are formed on the forward end of the outer tube and are designed to flex radially outward to allow the tampon to be expelled. It will be appreciated that the diameter of the applicator, the material from which it is formed, the basic configuration of the applicator, the size and shape of the tampon positioned in the applicator, as well as the ease of opening the forward end of the applicator will all influence the force required to expel the tampon therefrom. The expulsion force should be kept reasonably low to permit proper functioning of the applicator.

While many have tried to design and manufacture tampon applicators which are more comfortable to use, there still remains a need for a more comfortable tampon applicator. One way to manufacture a more comfortable tampon applicator is to reduce the force required to expel a tampon through the insertion tip.

Now a tampon applicator has been invented having an insertion tip which requires a minimum amount of force to expel a tampon through it. The invention also relates to an apparatus and method of reducing the force required to expel a catamenial tampon through the insertion tip.

SUMMARY OF THE INVENTION

Briefly, this invention relates to an apparatus and method for reducing the force required to expel a catamenial tampon from a tampon applicator. The invention also relates to the tampon applicator itself. The tampon applicator includes a first member which is capable of housing an absorbent tampon. The first member has an inside diameter, first and second spaced apart ends, and an insertion tip formed adjacent to the first end. The insertion tip closes at least a portion of the first end of the first member and facilitates insertion of the tampon applicator into a woman's vagina. The insertion tip has at least some of the paper fibers stretched and/or broken so as to allow it to be opened with a minimum amount of expulsion force.

The apparatus includes a first punch having an outside diameter which is sized slightly less than the inside diameter of the first member. This enables the first punch to slide within the first member from the second end toward the first end. The first punch has a forward end which is capable of opening the insertion tip. The apparatus also includes a second punch having a forward end with an outside diameter which is sized larger than the inside diameter of the first member. The second punch is capable of entering the opened insertion tip and expanding at least a portion of the inside diameter of the first member.

The method includes using the above-mentioned apparatus as well as the step of reclosing and forming the insertion tip such that the tip can be later reopened at a reduced expulsion force than that required to initially open it.

The general object of this invention is to provide an apparatus and method of reducing the force required to expel a catamenial tampon from a tampon applicator. A more specific object of this invention is to provide a tampon applicator having an insertion tip which requires a minimum amount of force to expel a catamenial tampon therethrough.

Another object of this invention is to provide an apparatus which can be used to open and expand an insertion tip formed on the forward end of a tampon applicator, such that after the tip is reclosed, a reduced force is needed to reopen it.

A further object of this invention is to provide a paper tampon applicator with an insertion tip which has at least some of the paper fibers of the tip stretched and/or broken.

Still further, an object of this invention is to provide a method of opening up an insertion tip and expanding at least a portion of the inside diameter of the outer tube such that a tampon can be expelled through the insertion tip with a minimum amount of force.

Other objects and advantages of the present invention will become more apparent to those skilled in the art in view of the following description and the accompanying drawings.

DETAILED DESCRIPTION OF THE PREFERRED EMBODIMENT

Figure 1:
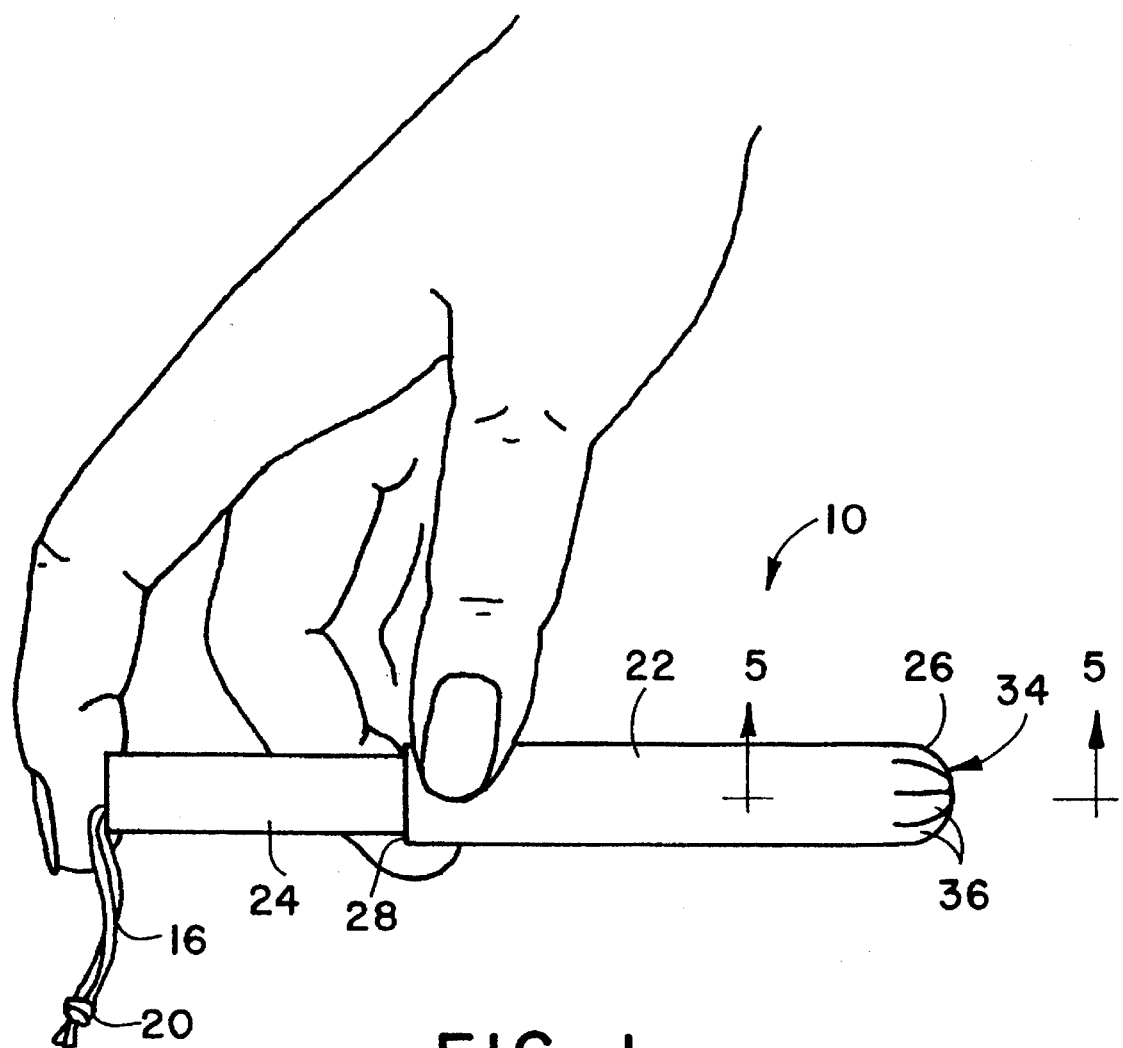
FIG. 1 is a side elevational view of a tampon applicator including first and second members telescopically assembled and showing an insertion tip formed on the forward end of the first member.
Figure 2:
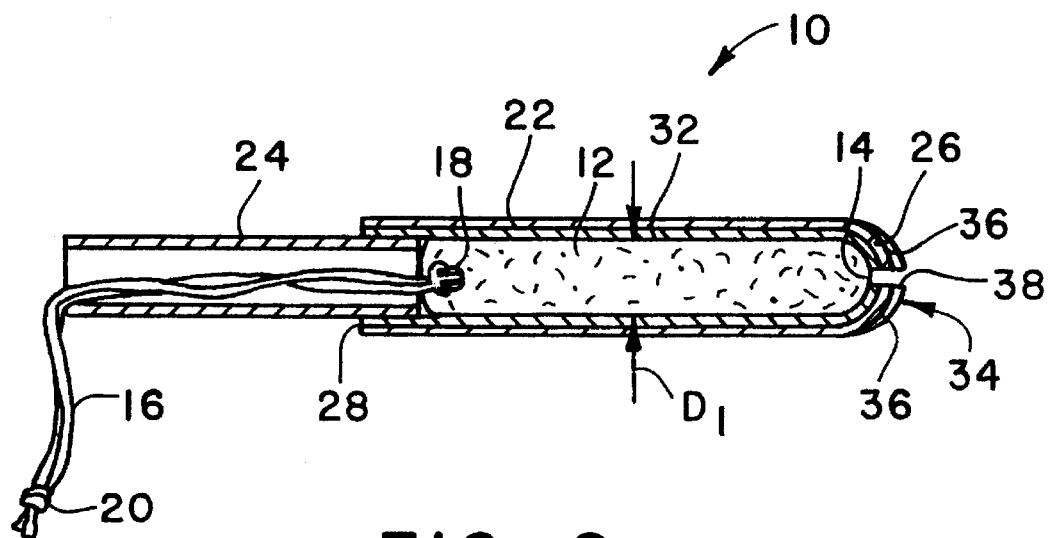
FIG. 2 is a cross-sectional view of the tampon applicator shown in FIG. 1 depicting the presence of a tampon housed in the first member.

Referring to FIGS. 1 and 2, a tampon applicator 10 is shown which is designed to house a catamenial tampon 12 and provide a comfortable means of inserting the tampon 12 into a woman's vagina. A tampon is an absorbent member primarily designed to be worn by a woman during her menstrual period to absorb menses, blood and other body fluid. The tampon 12 can be made from natural or synthetic fibers including cellulose fibers such as cotton or rayon, or artificial fibers such as polyester, polypropylene, nylon or blends thereof. A blend of cotton and rayon fibers works well.

The tampon 12 is normally compressed into the form of a cylinder and can have a blunt, rounded or shaped forward end 14. The tampon 12 commonly has a withdrawal string 16 fastened to an end thereof which serves as a means for withdrawing the soiled tampon from the woman's vagina. The withdrawal string 16 can be looped through an aperture 18 formed transversely through the tampon 12 or be attached in some other manner. The withdrawal string 16 can have a knot 20 formed at it's free end to assure that the withdrawal string 16 will not separate from the tampon 12.

The tampon applicator 10 can be a single member or include two or more members. For purposes of this discussion, the tampon applicator 10 will be described as a two piece telescopic assembly which includes a first member 22 and a second member 24. Both members 22 and 24 are depicted as being hollow tubes with the inner tube 24 being sized to telescopically slide within the outer tube 22. It should be noted that the second member 24 does not have to be a hollow tube but can be a solid stick. It also is not necessary for the second member 24 to be sized to slide within the first member 22, for example, the second member 24 can be a stick which can be directly attached to the tampon 12.

In the two piece tubular design, it is preferred that both the first and second members 22 and 24, respectively, be formed from paper. The term "paper" is used herein to include paper, paperboard, cardboard, thermoplastic film, a combination thereof, or from some other materials having similar characteristics to those identified above. The paper can be coated with a wax or a water-insoluble polymer to render it water-resistant. The first and second members 22 and 24, respectively, should have sufficient strength and rigidity to prevent collapse under normal vaginal pressures. Adequate strength and rigidity can be obtained by forming the first and second members 22 and 24, respectively, into elongated cylindrical shapes by spirally winding, convolutely winding, longitudinally seaming or by rolling and overlapping the material upon itself.

The first member 22, commonly referred to as an outer tube, should be constructed to have a relatively constant inside diameter $D_1$ along a major portion of it's overall length. The length of the first member 22 is normally between about 2 inches to about 4 inches (about 50.8 mm to about 101.6 mm), preferably, about 3 inches (about 76.2 mm). The inside diameter $D_1$ should be large enough to house the absorbent tampon 12. Typically, catamenial tampons have a diameter of between about 10 mm to about 20 mm. The first member 22 also has first and second spaced apart ends 26 and 28, respectively. The first end 26 corresponds to the forward end of the tampon applicator 10 and the second end 28 represents the opposite end into which the second member 24 is slidably positioned.

The first member 22 can be formed from one or more distinct layers of material. In FIG. 2, the first member 22 is depicted as being constructed of two distinct layers 30 and 32. The layers 30 and 32 can be made from the same or different materials or be made from similar material having different properties. For example, each layer 30 and 32 can have a different thickness, board weight, density, etc. The first and second members 22 and 24, respectively, can be formed from one to eight separate and distinct layers, preferably, between two to five layers, with two or three layers being the most preferred.

The outside or exterior layer 30 can be formed from a thin coated paperboard while one or more inner layers 32 can be formed from a non-coated material having a higher board weight. The exterior layer 30 can consist of a high gloss, coated paper which is water-degradable or water-dispersible. The coating could also have different finishes, such as a satin finish or a semi-gloss finish. The coating on the first member 22 can be selected from a wide variety of materials. Some specific coatings include polyethylene, polypropylene, polyvinylidene chloride and polychloride alcohol.

The layers 30 and 32 can be held together by an adhesive, such as glue, or by heat, pressure, ultrasonics, etc. The adhesive can be either water-soluble or water-insoluble. A water-soluble adhesive is preferred for environmental reasons in that the first and second members 22 and 24 can break apart when immersed in water.

As stated above, the first member 22 is sized and configured to house the absorbent tampon 12. The inside diameter of the first member 22 is sized to accommodate typical size tampons. Normally, the inside diameter of the first member 22 is less than about 0.75 inches (about 19 mm) and preferably less than about 0.625 inches (about 16 mm). Although the exterior diameter of tampons do vary, most tampons utilized by women have an external diameter of less than about 0.75 inches (about 19 mm). However, if one desires to use the applicator 10 to administer medication to an animal, such as a farm animal, larger size tampons 12 could be used.

The first member 22 can be a straight, elongated cylindrical tube formed on a central longitudinal axis. It is also possible to form the first member 22 into an arcuate shape. The arcuate or curved shape can assist in providing comfort when inserting the first member 22 into a woman's vagina. With a curved tampon applicator, it is possible to employ a curved tampon which again may be more comfortable for some women to use since the shape of the tampon may better fit the curvature of a woman's vagina.

Figure 3:
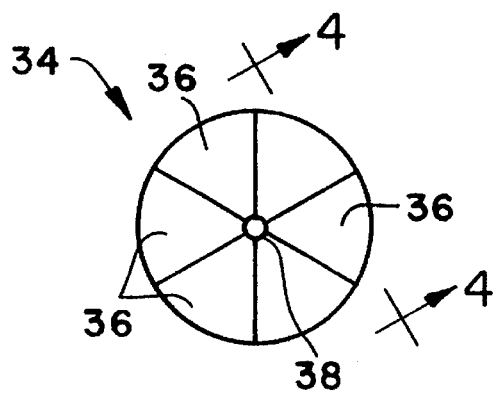
FIG. 3 is an enlarged right end view of FIG. 1 showing the insertion tip.
Figure 4:
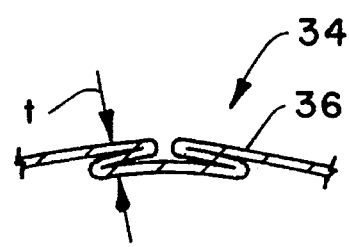
FIG. 4 is a schematic view of a pleat taken along line 4—4 of FIG. 3 depicting the shape and thickness of a pleat.
Figure 5:
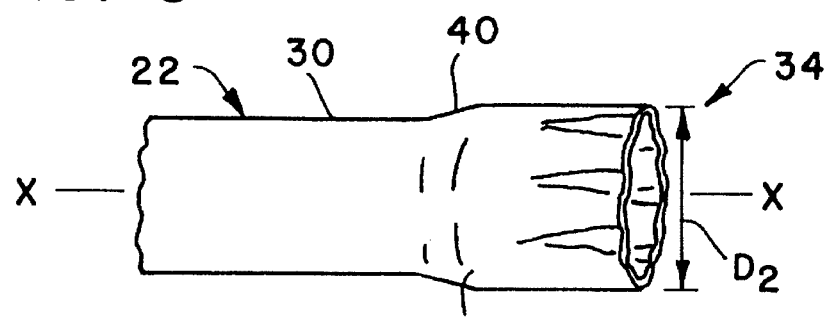
FIG. 5 is a perspective view of the first member showing the insertion tip in an open and expanded condition.

Referring to FIGS. 3–5, an insertion tip 34 is integrally formed on the first end 26 of the first member 22 and extends outwardly therefrom. The insertion tip 34 is designed to facilitate insertion of the first member 22 into a woman's vagina in a comfortable manner. The insertion tip 34 can be rounded, semi-spherical or frusto-conical in shape. Other nose or dome-like shapes can also be utilized. The rounded configuration of the insertion tip 34 functions to prevent the forward end of the tampon 12 from exerting an abrasive action upon the wall of the vagina as would be the case if it was uncovered.

The insertion tip 34 can be constructed of the same material which was used to form the first member 22 or it can be constructed out of a different material. The insertion tip 34 can also be thinner and/or have a lower board weight than the first member 22. The insertion tip 34 should be thin, soft and flexible and can contain a coating or be impregnated with a solution which inhibits substantial absorption of vaginal fluids. The coating can be an oil, a wax or formed from some other acceptable organic compound.

The insertion tip 34 includes a plurality of flexible pleats 36 arranged in a radial fashion. The pleats 36 can at least partially or fully enclose the forward end of the tampon 12. Each pleat 36 has a length of between about 0.25 inches to about 1 inch (about 6.35 mm to about 25.4 mm), preferably about 0.5 inches (about 12.7 mm). Each pleat 36 has an apex which terminates at or adjacent to the center forward end of the insertion tip 34. Any number of pleats 36 can be used, with from three to ten pleats 36 being sufficient. Six pleats 36 are depicted in FIG. 3.

Optionally formed at the apex of the insertion tip 34 can be an aperture 38. The aperture 38 is aligned along the central longitudinal axis. The aperture 38 serves to provide a visual means of inspecting the tampon applicator 10 to make sure a tampon 12 is positioned in the first member 22. The aperture 38 can be of any size but preferably is sized to be about 10 percent to about 30 percent of the outer diameter of the first member 22, preferably about 20 percent of the outer diameter of the first member 22. When an aperture 38 is not present, the pleats 36 will completely enclose the forward end of the tampon 12.

Referring to FIG. 4, each pleat 36 is obtained by folding the material upon itself so that when the pleat 36 is opened or unfolded it will occupy a much larger surface area. The thickness of the material forming the insertion tip 34 can be less than the thickness of the first member 22. The insertion tip 34 has a thickness of between about 0.03 mm to about 0.5 mm. In the folded condition, each pleat 36 has a thickness, indicated by the letter "t" which should be less than about 1.0 mm, preferably between about 0.75 mm to about 0.85 mm. Each pleat 36 is capable of expanding radially outward as the tampon 12 is expelled from the first member 22 by movement of the second member 24 therein. The pleats 36 will start to open as the tampon 12 is pushed forward by the second member 24 and a force is exerted on their inside surface. The pleats 36 are capable of opening to a diameter which is equal to or larger than the diameter of the first member 22. This expanded size allows the tampon 12 to be expelled from the first member 22 with a minimum amount of force.

Referring to FIG. 5, the insertion tip 34 is shown in an open condition having been initially pleated and formed into a rounded nose shaped end as depicted in FIG. 2. The insertion tip 34 is then expanded to an inside diameter $D_2$ which is slightly larger than the inside diameter $D_1$ of the first member 22. This difference in diameter can range from between about 0.001 of an inch to about 0.025 of an inch (about 0.025 mm to about 0.63 mm), preferably from about 0.005 of an inch to about 0.015 of an inch (about 0.127 mm to about 0.381 mm) when the first member 22 has an outside diameter of less than about 0.75 inches (about 19 mm). The apparatus and method of forming the diameter $D_2$ will be explained below. The transition of the larger diameter $D_2$ to the smaller diameter $D_1$ should be gradual and smooth. The transitional area, denoted as 40 in FIG. 5, may not show up on the exterior surface of the first member 22. The thickness of the layers 30 and 32 as well as the difference between the diameters $D_1$ and $D_2$ will determine if any enlargement at location 40 will be present. The larger diameter $D_2$ occurs by the stretching and/or breaking of the fibers forming the paper layers 30 and 32. After the insertion tip 34 has been enlarged it is again pleated and reformed back into it's original configuration. In the reclosed shape, the outside diameter of the insertion tip 34 will be identical to the outside diameter of the first member 22. Likewise, the inside diameter $D_2$ of the insertion tip 34 will be equal to the inside diameter $D_1$ of the first member 22.

It is contemplated that the first member 22 will be formed into a hollow, cylindrical tube having a relatively constant inside diameter $D_1$. The first end 26 of the tube 22 will then be crimped, pleated and formed into the generally semi-spherical shape insertion tip 34 using pleating and forming tools known to those skilled in the art. After the insertion tip 34 is formed, it is initially opened and expanded using special tools. The insertion tip 34 is then reformed using pleating and forming tools such that it is capable of being reopened at a later time at a lower expulsion force than that required to initially open it. The insertion tip 34 is reopened after a tampon has been positioned in the first member 22.

It has been found that by initially opening the insertion tip 34, expanding it's inside diameter to $D_2$, and then reclosing and reforming the insertion tip 34 to it's original size, that the force required to expel the tampon 12 from the first member 22 is substantially reduced. This reduction in force can be at least 25 percent lower than the force required to initially open the insertion tip 34. Preferably, this force is at least 40 percent lower, and most preferably, is at least 50 percent lower than the force required to initially open the insertion tip 34. This significant reduction in force is accomplished by expanding the inside diameter of the insertion tip 34 such that the fibers forming the layers 30 and 32 are stretched, fractured, reoriented and/or broke and thereby require less force to reopen.

Figure 6:
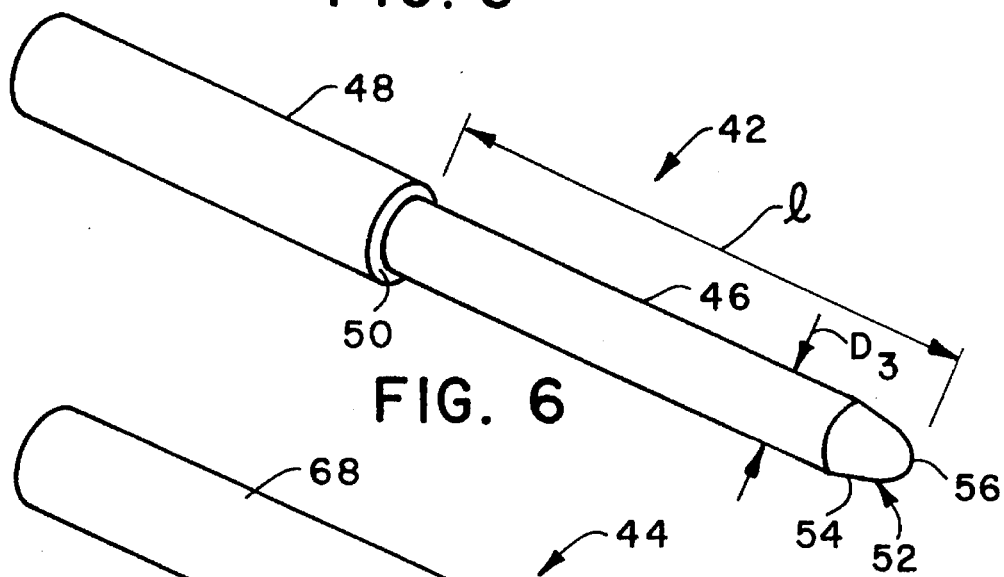
FIG. 6 is a perspective view of a first punch used to open the insertion tip.
Figure 7:
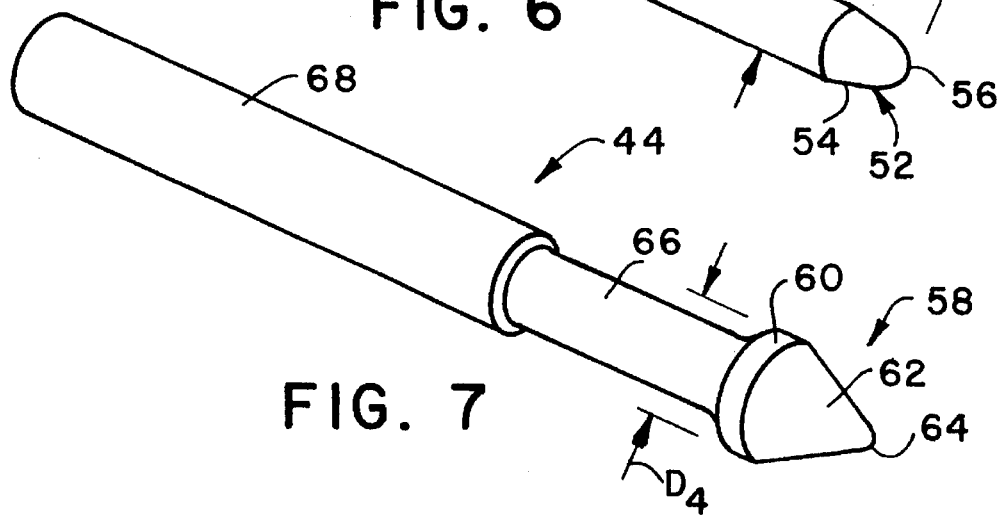
FIG. 7 is a perspective view of a second punch used to expand at least a portion of the inside diameter of the first member.

Referring to FIGS. 6 and 7, the apparatus for opening and enlarging the diameter of the insertion tip 34 is shown. The apparatus includes a first punch 42 and a second punch 44. The first or opening punch is an elongated, cylindrical member having an outside diameter $D_3$ which is less than that of the inside diameter $D_1$ of the first member 22. This difference in size permits the first punch 42 to slide within the inside diameter $D_1$ of the first member 22. The outside diameter $D_3$ of the first punch 42 can be as little as about 0.001 of an inch (about 0.025 mm) less than the inside diameter $D_1$ of the first member 22. Preferably, the outside diameter $D_3$ of the first punch 42 is about 0.001 to about 0.015 of an inch (about 0.025 to about 0.381 mm) less than the inside diameter $D_1$ of the first member 22. Most preferably, the outside diameter $D_3$ of the first punch 42 is at least about 0.005 of an inch (about 0.127 mm) less than the inside diameter $D_1$ of the first member 22.

The first punch 42 has a first section 46 and a second section 48. The two sections 46 and 48 can be machined from a single elongated shaft or rod. The first section 46 has a constant outside diameter $D_3$ while the second section 48 has a larger outside diameter. The two sections 46 and 48 meet to form a shoulder 50. Formed on the distal end of the first section 46 is a forward end 52 which is capable of opening the insertion tip 34 from the inside. The forward end 52 includes a tapered section 54 having a rounded nose 56. However, other semi-spherical, frusto-conical, rounded or pointed configurations can be utilized, if desired. The overall configuration of the forward end 52 should approximately match the inside shape of the insertion tip 34 and be generally of about the same diameter for best results.

The length "l" of the first section 46, which has the diameter $D_3$, should be longer then the overall length of the first member 22. The reason for this is that the first punch 42 is designed to be inserted into the second end 28 of the first member 22 and slid completely therethrough so that it can contact and fully open the insertion tip 34. Preferably, the first section 46 will be long enough to extend past the insertion tip 34. In operation, it is envisioned that the second section 48 of the first punch 42 will be tightly secured to a reciprocal chuck and the first section 46 will be brought into axial alignment with the second end 28 of the first member 22. The first punch 42 will slide through the first member 22 and contact and open the insertion tip 34. As this occurs, the second end 28 of the first member 22 will contact the shoulder 50 of the first punch 42 and be prevented the first member 22 from moving any further along the length of the first punch 42.

It should be noted to those skilled in the art, that alternatively, the first punch 42 can be held stationary and the first member 22 can be axially moved relative to the first punch. Once the insertion tip 34 is opened, the first member 22 is removed from the first punch 42. This can be accomplished by withdrawing the first punch 42 from the first member 22, withdrawing the first member 22 from the first punch 42, or by simultaneously withdrawing both members 22 and 42 from one another.

The second or expanding punch 44 is an elongated, cylindrical member which has a forward end 58. The forward end 58 is shown in the shape of a teardrop, although other shapes may work as well. The teardrop shape includes a circular rim 60 which tapers down to form a frusto-conical surface 62 which terminates into a rounded point 64. Located rearward of the circular rim 60 is a neck portion 66 which is relatively small in diameter. The forward end 58 has an outside diameter $D_4$ which is larger than the inside diameter $D_1$ of the first member 22. The outside diameter $D_4$ of the forward end 58 should be at least about 0.002 of an inch (about 0.050 mm) larger than the inside diameter $D_1$ of the first member 22. Preferably, the outside diameter $D_4$ of the forward end 58 will be at least about 0.015 of an inch (about 0.381 mm) larger than the inside diameter $D_1$ of the first member 22.

The second punch 44 is designed to have the forward end 58 inserted into the first end 26 of the first member 22 after the insertion tip 34 has been initially opened by the first punch 42. The forward end 58 will expand at least a portion of the inside diameter $D_1$ of the first member 22 to the larger inside diameter $D_2$. This expansion causes the fibers to stretch, fracture, reorient and/or break thereby weakens the material forming the insertion tip 34. The forward end 58 of the second punch 44 is inserted into the first member 22 a sufficient distance so that the insertion tip 34 will acquire a larger inside diameter $D_2$. Typically, this is a distance of at least about 0.5 inches (about 12.7 mm). Preferably, the forward end 58 of the second punch 44 is inserted into the first end 26 of the first member 22 a depth which is equal to or extends beyond the length of the pleats 36.

The second punch 44 also has a second section 68 which can be secured in a chuck mounted to an arbor press. The second punch 44 can then be reciprocated relative to a stationary first member 22. It is also possible to hold the second punch 44 stationary and move the first member 22 relative to it as was explained above with reference to the first punch 42.

METHOD

Figure 8:
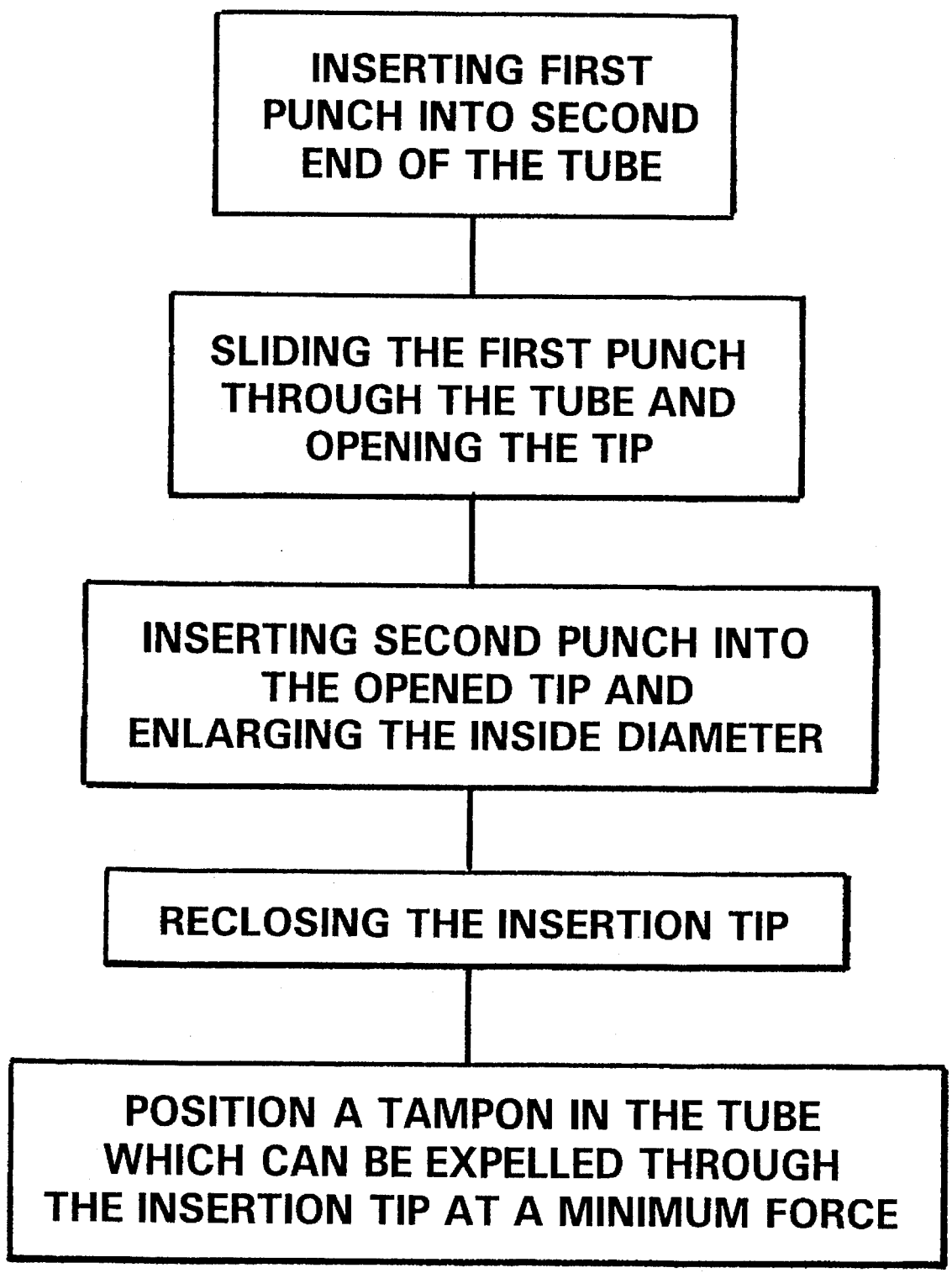
FIG. 8 is a flow diagram depicting the method of opening the insertion tip, expanding the inside diameter of the first member, reclosing the insertion tip and positioning a tampon in the first member.

The method of reducing the force required to expel a tampon 12 from a tampon applicator 10 will be explained with reference to the flow diagram depicted in FIG. 8. Starting with the first member or outer tube 22 having an insertion tip 34 formed adjacent to the first end 26, the method is as follows. The first punch 42 is inserted into the second end 28 of the outer tube 22 and is slid through it until it contacts the insertion tip 34. The first punch 42 is then pushed through the pleats 36 and radially expands the insertion tip 34 to a diameter which is at least 90% of the inside diameter $D_1$ of the outer tube 22. The first punch 42 is then withdrawn from the outer tube 22 and the second punch 44 is inserted into the opened insertion tip 34 from the first end 26. The forward end 58 of the second punch 44, with it's larger diameter $D_4$, causes the inside diameter of the insertion tip 34 to expand to a diameter $D_2$ which will be larger than the initial inside diameter $D_1$. The diameter $D_2$ will be approximately equal to the diameter $D_4$. The forward end 58 of the second punch 44 is inserted into the first end 26 of the outer tube 22 a distance which, preferably, should be equal to or extend beyond the length of each pleat 36. This causes a portion of the inside diameter $D_1$ of the outer tube 22 to expanded to $D_2$. The second punch 44 is then withdrawn and the insertion tip 34 is reclosed. In the reclosed configuration, the insertion tip 34 will have pleats 36 and be reformed into it's rounded shape.

An absorbent tampon 12 is then inserted into the second end 26 of the outer tube 22 and the inner tube 24 is telescopically assembled with the outer tube 22. This assembly has the withdrawal string 16 passing through the inner tube 24 and extending out of the free end thereof. The assembly is pictured in FIG. 1. This assembly is ready for use by the consumer. During use, the consumer will position the outer tube 22 in her vagina and push on the free end of the inner tube 24. Such action causes the tampon 12 to move forward and contact the insertion tip 34. As the tampon 12 is moved further forward, the pleats 36 forming the insertion tip 34 will radially open with a minimum amount of force. The insertion tip 34 will be open to a sufficient size to allow the tampon 12 to be freely expelled into the vaginal cavity. The force required to expel the tampon 12 will be less than that required to initially open the insertion tip 34 by the first punch 42. With the tampon 12 inserted in the vaginal cavity, the tampon applicator 10 is withdrawn and properly discarded.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An apparatus for reducing the force required to expel a catamenial tampon from a tampon applicator, said applicator including a first member which is capable of housing a tampon, said first member having an inside diameter, first and second spaced apart ends, and an insertion tip formed adjacent to said first end, said apparatus comprising:

a) a first punch having an outside diameter which is sized to slide within said first member and having a forward end which is capable of opening said insertion tip; and b) a second punch having a forward end with an outside diameter which is sized larger than said inside diameter of said first member, said second punch capable of entering said opened insertion tip and expanding at least a portion of said inside diameter of said first member.

2. The apparatus of claim 1 wherein said tampon applicator is paper.

3. The apparatus of claim 2 wherein said first punch is an elongated, cylindrical member having a diameter at least 0.001 of an inch less than said inside diameter of said first member.

4. The apparatus of claim 2 wherein said first punch has a diameter at least 0.005 of an inch less than said inside diameter of said first member.

5. The apparatus of claim 2 wherein said forward end of said first punch comprises a tapered section having a rounded nose.

6. The apparatus of claim 1 wherein said first member has a predetermined length and said first punch has a length which is longer than said first member.

7. The apparatus of claim 1 wherein said forward end of said second punch has a teardrop shape.

8. The apparatus of claim 1 wherein said forward end of said second punch has an outside diameter which is at least 0.002 of an inch larger than said inside diameter of said first member.

9. The apparatus of claim 8 wherein said forward end of said second punch has an outside diameter which is at least 0.015 of an inch larger than said inside diameter of said first member.

10. An apparatus for reducing the force required to expel a catamenial tampon from a paper tampon applicator, said tampon applicator including a first member which is capable of housing a tampon, said first member having an inside diameter, first and second spaced apart ends, and an insertion tip formed adjacent to and at least partially closing said first end, said apparatus comprising:

a) a first elongated punch having an outside diameter which is sized slightly less than said inside diameter of said first member to enable said first punch to slide within said first member from said second end toward said first end, and having a forward end which is capable of opening said insertion tip; and b) a second punch having a teardrop shaped forward end with an outside diameter which is sized larger than said inside diameter of said first member, said second punch capable of entering said opened insertion tip and expanding at least a portion of said inside diameter of said first member.

11. The apparatus of claim 10 wherein said first punch has a diameter at least 0.005 of an inch less than said inside diameter of said first member.

12. The apparatus of claim 10 wherein said forward end of said first punch comprises a tapered section having a rounded nose.

13. The apparatus of claim 10 wherein said forward end of said second punch has an outside diameter which is at least 0.002 of an inch larger than said inside diameter of said first member.

14. A method of reducing the force required to expel a catamenial tampon from a tampon applicator, said applicator including a first member which is capable of housing a tampon, said first member having an inside diameter, first and second spaced apart ends, and an insertion tip formed adjacent to said first end, said method comprising the steps of:

a) inserting a first punch into said second end of said first member;

b) sliding said first punch through said first member and opening said insertion tip; and c) inserting a second punch into said opened insertion tip, said second punch having a forward end with an outside diameter which is sized larger than said inside diameter of said first member whereby at least a portion of said inside diameter of said first member is expanded.

15. The method of claim 14 wherein said first punch opens said insertion tip to at least 90% of said inside diameter of said first member.

16. The method of claim 14 wherein said insertion tip is reclosed after said first end has been expanded.

17. The method of claim 14 wherein a tampon is positioned in said first member and said tampon can be expelled through said insertion tip at an expulsion force which is less than that required to initially open said insertion tip with said first punch.

18. The method of claim 14 wherein said second punch is inserted at least 0.5 inches into said first member.

19. The method of claim 14 wherein said second punch is inserted into said first member beyond the length of said insertion tip.

20. A method of reducing the force required to expel a catamenial tampon from a tampon applicator, said applicator including a first member which is capable of housing a tampon, said first member having an inside diameter, first and second spaced apart ends, and an insertion tip formed adjacent to and at least partially closing said first end, said method comprising the steps of:

a) inserting a first punch into said second end of said first member;

b) sliding said first punch through said first member and expanding said insertion tip;

c) inserting a second punch into said opened insertion tip, said second punch having a forward end with an outside diameter which is sized larger than said inside diameter of said first member whereby at least a portion of said inside diameter of said first member is expanded;

d) reclosing said insertion tip; and e) positioning a tampon in said first member, said tampon capable of being expelled through said insertion tip at an expulsion force which is less than that required to initially open said insertion tip.

21. The method of claim 20 wherein said second punch is inserted at least 0.5 inches into said first member.

22. The method of claim 20 wherein said second punch is inserted into said first member beyond the length of said insertion tip.

23. A tampon applicator comprising;

a) a first member capable of housing an absorbent tampon, said first member having an inside diameter, and first and second spaced apart ends; and b) an insertion tip formed adjacent to and at least partially closing said first end, said insertion tip having been opened, expanded and reclosed prior to positioning said absorbent tampon into said first member.

24. The tampon applicator of claim 23 wherein said first member is paper.

25. The tampon applicator of claim 23 wherein said insertion tip is pleated and formed into a rounded shape.

26. A tampon applicator comprising;
a) a first member capable of housing an absorbent tampon, said first member having an inside diameter, and first and second spaced apart ends; and
b) a pleated insertion tip formed adjacent to and at least partially closing said first end, said insertion tip having been opened, expanded and reclosed prior to positioning said absorbent tampon into said first member, and said insertion tip can be reopened at an expulsion force which is less than that required to initially open said tip.

27. The tampon applicator of claim 26 wherein said first member is paper.

28. The tampon applicator of claim 26 wherein said insertion tip is pleated and formed into a rounded shape.

* * * * *